United States Patent [19]
Bourzat et al.

[11] Patent Number: 4,960,779
[45] Date of Patent: Oct. 2, 1990

[54] PYRROLE DERIVATIVES, AND PHARMACEUTICAL COMPOSITIONS WHICH CONTAIN THEM AND PHARMACOLOGICAL METHODS OF USE

[75] Inventors: Jean-Dominique Bourzat, Paris; Marc Capet, Thiais; Claude Cotrel, Paris, all of France; Richard Labaudiniere, Bruehl, Fed. Rep. of Germany; Philippe Pitchen, Brentwood, England; Gerard Roussel, Soisy S/Seine, France

[73] Assignee: Rhone-Poulenc Sante, Antony, France

[21] Appl. No.: 360,122

[22] Filed: Jun. 1, 1989

Related U.S. Application Data

[63] Continuation-in-part of Ser. No. 126,520, Nov. 30, 1987, abandoned.

[30] Foreign Application Priority Data

Dec. 2, 1986 [FR] France .................. 86 16795

[51] Int. Cl.$^5$ ............... C07D 470/104; A61K 31/435
[52] U.S. Cl. .................... 514/300; 514/312; 514/313; 514/339; 546/122; 546/153; 546/159; 546/162; 546/272
[58] Field of Search ............... 546/122, 153, 159, 162, 546/272; 514/300, 312, 313, 339

[56] References Cited

U.S. PATENT DOCUMENTS 3,884,921 5/1975 Cotrel et al. ............... 546/159
4,244,966 1/1981 Lippman et al. ............ 514/416
4,590,189 5/1986 Hiraga et al. .............. 546/122

FOREIGN PATENT DOCUMENTS 8403089 8/1984 PCT Int'l Appl. .

Primary Examiner—Alan L. Rotman
Assistant Examiner—J. K. McKane

Attorney, Agent, or Firm—Stevens, Davis, Miller & Mosher

[57] ABSTRACT

Pyrrole derivatives of formula (I):

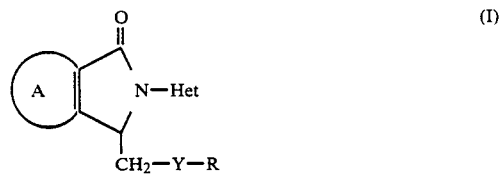

in which A forms with the pyrrole ring an isoindoline, 6,7-dihydro-5H-pyrrolo[3,4-b]pyrazine, 2,3,6,7-tetrahydro-5H-[1,4]oxathiino[2,3-c]pyrrole or 2,3,6,7-tetrahydro-5H-[1,4]dithiino[2,3-c]pyrrole ring-system, Het= naphthyridinyl, pyridyl or quinolyl which are unsubstituted or substituted with halogen, (1 to 4 C) alkyl, (1 to 4 C) alkyloxy, (1 to 4 C) alkylthio or $CF_3$, Y=CO, C=NOH or CHOH and R=(3 to 10 C) alkenyl, alkyl which is unsubstituted or substituted with OH, alkyloxy, alkylthio, (3 to 6 C) cycloalkyl, $NH_2$, alkylamino, dialkylamino, alkylcarbonylamino, piperazinyl, piperidyl, 1-azetidinyl, morpholino, pyrrolidinyl, carbamoyl, alkylcarbamoyl, dialkylcarbamoyl, (1-piperazinyl)carbonyl, piperidinocarbonyl, pyrrolidinocarbonyl, phenyl, pyridyl, 1-imidazolyl or alternatively R=2- or 3-pyrrolididnyl, 2-, 3- or 4-piperidyl, (3 to 6 C) cycloalkyl or phenyl which is unsubstituted or substituted with halogen, (1 to 4 C) alkyl, (1 to 4 C) alkyloxy, (1 to 4 C) alkylthio, the said alkyl radicals and portions containing, except where specifically stated, 1 to 10 C, and the piperazinyl, piperidino, piperidyl, pyrrolidinyl, azetidinyl radicals being unsubstituted or substituted at any position by alkyl, alkylcarbonyl, benzyl or hydroxyalkyl, or can alternatively form a lactam group with the nitrogen atom of the ring, and their salts and optical isomers are useful as anxiolytics.

12 Claims, No Drawings

PYRROLE DERIVATIVES, AND PHARMACEUTICAL COMPOSITIONS WHICH CONTAIN THEM AND PHARMACOLOGICAL METHODS OF USE

This Application is a continuation-in-Part of Application Ser. No. 126520 filed Nov. 30th 1987, now abandoned.

The present invention provides new pyrrole derivatives of the general formula:

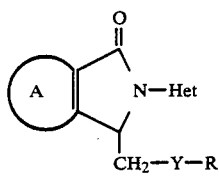

in which A forms with the pyrrole ring an isoindoline, 6,7-dihydro-5H-pyrrolo[3,4-b]pyrazine, 2,3,6,7-tetrahydro-5H-[1,4]oxathiino[2,3-c]pyrrole or 2,3,6,7-tetrahydro-5H-[1,4]dithiino[2,3-c]pyrrole ring-system, Het denotes a naphthyridinyl, pyridyl or quinolyl radical, which is unsubstituted or substituted with a halogen or a (1 to 4 C.) alkyl, (1 to 4 C.) alkyloxy, (1 to 4 C.) alkylthio or trifluoromethyl radical, Y denotes a CO, C=NOH or CHOH radical and R denotes a straight- or branched-chain alkenyl radical containing 3 to 10 carbon atoms or an alkyl radical which is unsubstituted or substituted by hydroxy, alkyloxy, alkylthio, cycloalkyl of 3 to 6 carbon atoms, amino, alkyl-amino, dialkyl-amino, alkylcarbonylamino, piperazinyl, piperidyl, 1-azetidinyl, morpholino, pyrrolidinyl, carbamoyl, alkylcarbamoyl, dialkylcarbamoyl, (1-piperazinyl)-carbonyl, piperidinocarbonyl, pyrrolidinocarbonyl, phenyl, pyridyl or 1-imidazolyl, or R denotes a 2- or 3- pyrrolidinyl or 2-, 3- or 4- piperidyl radical, cycloalkyl of 3 to 6 carbon atoms or phenyl which is unsubstituted or substituted, by halogen, (1 to 4 C) alkyl, (1 to 4 C) alkyloxy or (1 to 4 C) alkylthio, the aforesaid alkyl radicals being straight- or branched-chain radicals and containing, except where specifically stated, 1 to 10 carbon atoms, and the said piperazinyl, piperidino, piperidyl, pyrrolidinyl and azetidinyl radicals being unsubstituted or substituted at any position by alkyl, alkylcarbonyl, benzyl or hydroxyalkyl, or can alternatively form a lactam group with the nitrogen atom of the ring, and, where they exist, their pharmaceutically acceptable salts and optical isomers.

According to a feature of the invention, the compounds of formula (I) in which Y denotes a CO radical and the other symbols are as defined above, except that Het does not denote a 1,8-naphthyridin-2-yl radical substituted by halogen at the 7-position, are prepared by the action of a ketone of formula:

$$CH_3-CO-R \quad (II)$$

in which R is as defined above, with a 3-hydroxyisoindolinone of formula:

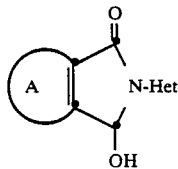

in which A and Het are as deFined above, except that Het does not denote a 1.8-naphthyridin-2-yl radical substituted at the 7-position by halogen.

The reaction is generally performed in a dipolar aprotic solvent such as dimethylformamide or N-methyl-2-pyrrolidone, in the presence of a base such as an alkali metal hydride, e.g. sodium hydride, at a temperature of between $-10°$ and $+60°$ C.

The products of general formula (III) may be prepared by application or adaptation of the methods described in Belgian Pat. Nos. 793,851, 835,325 and 815,019.

According to a further feature of the invention, the products of general formula (I) in which Y denotes a CO radical and the other symbols are as deFined above, except that Het does not denote a 1,8-naphthyridin-2-yl radical substituted at the 7-position by alkyloxy or alkylthio, are prepared by the action of a β-keto ester of formula:

$$\begin{array}{l}\overset{}{C}H_2COR \\ | \\ COOR_1 \end{array} \quad (IV)$$

in which $R_1$ denotes alkyl and R is as defined above, on a compound of formula:

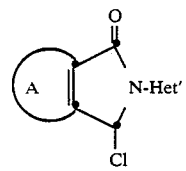

in which Het' has the definition given above for Het, but does not denote 1,8-naphthyridin-2-yl substituted at the 7-position by alkyloxy or alkylthio, and A is as defined above, followed by dealkylox)carbonylation of the intermediate ester formed.

The condensation of the keto-ester of formula (IV) with the compound of formula (V) is generally performed in an organic solvent in the presence of a base, e.g. in dimethylformamide or tetrahydrofuran in the presence of an alkali metal hydride such as sodium hydride, at a temperature of between 0° and 60° C. and preferably between 20° and 60° C.

The subsequent dealkyloxycarbonylation may be performed by any method known to those skilled in the art, in particular by alkaline saponification followed by an acidification and heating to a temperature of between 100° and 200° C., by acid hydrolysis and attendant decarboxylation at a temperature of between 100° and 200° C., or alternatively by heating in dimethyl sulphoxide in the presence of an alkali metal halide, e.g. lithium chloride, at a temperature of between 150° and 180° C.

The products of general formula (V) may be prepared by chlorination of a product of general formula (III).

The reaction is generally performed in the presence of a chlorinating agent such as sulphinyl chloride or phosphorus oxychloride, in the presence of catalytic amounts of dimethylformamide, at a temperature between 20° C. and the refluxing temperature of the reaction mixture, or any other agent known to those versed in the art which enable a hydroxy radical to be converted to a chloro radical without affecting the remainder of the molecule.

The products of general formula (I) prepared according to the two processes described above may be converted to other products of general formula (I) according to the usual methods. Thus:

(a) The products of general formula (I) in which Y denotes a C=NOH radical and the other symbols are defined as above may be obtained by the action of hydroxylamine on a product of general formula (I) in which Y denotes a CO radical and the other symbols are defined as above, in a solvent such as an aqueous-alcoholic mixture, at a temperature between 20° C. and the refluxing temperature of the reaction mixture.

(b) The products of general formula (I) in which Het denotes n 1,8-naphthyridin-2-yl radical substituted at the 7-position with a bromine or chlorine atom and the other symbols are defined as above may be prepared by the action of a halogenating agent such as phosphorus oxybromide or oxychloride on a product of general formula (I) in which Het denotes a 1,8-naphthyridin-2-yl radical substituted at the 7-position with an alkyloxy or alkylthio radical, and the other symbols are defined as above, working under reflux of the reaction mixture.

(c) The products of general formula (I) in which Y denotes a CHOH radical and the other symbols are defined as above may be prepared by the reduction of the corresponding products in which Y denotes a CO radical and the other symbols are defined as above.

The reduction is performed by any means known to those versed in the art for reducing a ketone to an alcohol without affecting the remainder of the molecule, e.g. by means of potassium borohydride in a mixture of alcohol and water at a temperature in the region of 20° C.

As will be realized by those versed in the art, some radicals falling within the definition of the symbol R are incompatible with the reactants employed during the reactions, and must be protected prior to carrying out the processes, or some phases of the processes, described above. This is the case, in particular, when the radical R contains primary or secondary amino groups or hydroxyl groups which are capable of giving rise to side reactions in the presence of metal hydrides or halogenating reagents. In this case, the said groups must be protected by any method known to those versed in the art, and then unblocked after reaction.

The new products of general formula (I) may be purified by the usual known methods, e.g. by crystallization, chromatography or successive extractions in acidic and basic medium.

The new products of general formula (I) may be converted to an addition salt with acids, by the action of an acid in water or in an organic solvent such as an alcohol, a ketone, an ether or a chlorinated solvent. The salt formed precipitates, where appropriate after concentration of its solution; it is separated by filtration or after settling has occurred.

The products of general formula (I) possess especially advantageous pharmacological properties, and have an anxiolytic, hypnotic, anticonvulsant, antiepileptic and muscle relaxant activity. Thus, they show appreciable affinity in vitro for benzodiazepine receptor sites at concentrations between 0.4 and 200 nM according to the technique described by J. C. BLANCHARD and L. JULOU, J. of Neurochemistry, 40, 601 (1983) modelled on the work of SQUIRES and BRAESTRUP, Nature, 266, 732 (1977).

In animals (mice), they have been shown to be active, at doses which are generally between 0.5 and 200 mg/kg orally, with respect to pentetrazole-induced convulsions according to a technique closely allied to that of EVERETT and RICHARDS, J. Pharmacol., 81, 402 (1944).

The products of general formula (I) and their salts possess, in addition, low toxicity. Their oral $LD_{50}$ is generally greater than 300 mg/kg in mice.

For medicinal use, the products of general formula (I) may be employed as they are or in the state of pharmaceutically acceptable salts, i.e. salts which are non-toxic at the dose$ at which they are used.

As examples of pharmaceutically acceptable salts, there may be mentioned the addition salts with inorganic acids, such as hydrochlorides, sulphates, nitrates and phosphates, or with organic acids, such as acetates, propionates, succinates, benzoates, fumarates, maleates, methanesulphonates, isethionates, theophyllineacetates, salicylates, phenolphthalinates and methylenebis($\beta$-oxynaphthoates), or substitution derivatives of these compounds.

Of special value are the products of general formula (I) in which A forms with the pyrrole ring an isoindoline or 6,7-dihydro-5H-pyrrolo[3,4-b]pyrazine ring-system, Het denotes a 1,8-naphthyridin-2-yl or 2-quinolyl radical which is unsubstituted or substituted by halogen, (1 to 4 C) alkyl, (1 to 4 C) alkoxy or (1 to 4 C) alkylthio, Y denotes a C=NOH or CHOH radical and R denotes straight- or branched-chain alkenyl oF 3 to 6 carbon atoms or an alkyl radical which is unsubstituted or substituted by hydroxy, alkyloxy, cycloakly of 3 to 6 carbon atoms, dialkylamino, dialkylcarbamoyl or phenyl, or R denotes 4-piperidyl or cyclohexyl, the said alkyl radicals being straight- or branched-chain radicals and containing, except where specifically stated, 1 to 10 carbon atoms each, and said piperidyl radical may be substituted at the 1-position by alkyl.

The following products are of very special value:
2-(7-chloro-1,8-naphthyridin-2-yl)-3-(5-methyl-2-oxohexyl)-1-isoindolinone
2-(7-methoxy-1,8-naphthyridin-2-yl)-3-(2-oxohexyl)-1-isoindolinone
2-(7-methoxy-1,8-naphthyridin-2-yl)-3-(5-methyl-2-oxohexyl)-1-isoindolinone
2-(7-methoxy-1,8-naphthyridin-2-yl)-3-(6-methyl-2-oxo-5-heptenyl)-1-isoindolinone
2-(7-methoxy-1,8-naphthyridin-2-yl)-3-(6-methyl-2-oxoheptyl)-1-isoindolinone
3-(3-cyclohexyl-2-oxopropyl)-2-(7-methoxy-1,8-naphthyridin-2-yl)-1-isoindolinone
2-(7-chloro-1,8-naphthyridin-2-yl)-3-(3-isopropoxy-2-oxopropyl)-1-isoindolinone
2-(7-chloro-2-quinolyl)-3-(5-methyl-2-oxohexyl)-1-isoindolinone
2-(7-fluoro-1,8-naphthyridin-2-yl)-3-(5-methyl-2-oxohexyl)-1-isoindolinone.

The examples which follow, illustrate the invention.

EXAMPLE 1

An oily suspension (50% by weight; 0.5 g) of sodium hydride is added in small portions at a temperature in the region of −5° C. to a solution, maintained under an argon atmosphere, of 3-hydroxy-2-(7-methoxy-1,8-naphthyridin-2-yl)-1-isoindolinone (1.6 g) in anhydrous dimethylformamide (20 cc), and the suspension obtained is stirred for 30 minutes at a temperature in the region of −5° C. A solution of 5-methyl-2-hexanone (1.2 g) in anhydrous dimethylformamide (5 cc) is then added and stirring is continued for 5 hours at a temperature in the region of 20° C. The reaction mixture is then poured into distilled water (200 cc) and extracted with dichloromethane (3×100 cc). The organic phases are combined, washed with distilled water (5×20 cc) and then concentrated to dryness under reduced pressure (2.7 kPa) at 40° C. The oily residue obtained is purified by chromatography on silica gel (15 g) contained in a column 1.5 cm in diameter [eluent: dichloromethane/methanol (99:1 by volume)]. Elution is first performed with 30 cc of solvent: the corresponding eluate is discarded; elution is then performed with 100 cc of solvent: the corresponding eluate is concentrated to dryness under reduced pressure (2.7 kPa) at 40° C. The residue obtained is recrystallized in ethyl acetate; 2-(7-methoxy-1,8-naphthyridin-2-yl)-3-(5-methyl-2-oxohexyl)-1-isoindolinone (1.3 g), m.p. 150° C., is thereby obtained.

EXAMPLE 2

Sodium hydride (0.7 g) is added in small portions at a temperature in the region of −5° C. to a solution, maintained under an argon atmosphere, of 3-hydroxy-2-(7-methoxy-1,8-naphthyridin-2-yl)-1-isoindolinone (8.0 g) in anhydrous dimethylformamide (125 cc). The suspension obtained is stirred for 30 minutes at a temperature in the region of −5° C. and then treated with a solution of 4-dimethylamino-2-butanone (3.5 g) in anhydrous dimethylformamide (5 cc). The mixture is stirred for 3 hours at a temperature in the region of 20° C., and is then poured into distilled water (500 cc) and extracted with dichloromethane (3×200 cc). The organic phases are combined, washed with distilled water (4×25 cc), dried over magnesium sulphate, filtered and then concentrated to dryness under reduced pressure (2.7 kPa) at 40° C. The oily residue obtained is dissolved in ethyl acetate (400 cc) and the solution obtained is extracted with 1 N aqueous hydrochloric acid solution (2×100 cc). The aqueous phases are combined, washed with ethyl acetate (50 cc), alkalinized with 10 N aqueous sodium hydroxide solution to a pH in the region of 11 and extracted with ethyl acetate (2×250 cc). The organic phases are combined, washed with distilled water (3×30 cc), dried over magnesium sulphate, filtered and then concentrated to dryness under reduced pressure (2.7 kPa) at 60° C. After recrystallization in acetonitrile, 3-(4-dimethylamino-2-oxobutyl)-2-(7-methoxy-1,8-naphthyridin-2-yl)-1-isoindolinone (2.6 g), m.p. 140° C., is obtained.

4-Dimethylamino-2-butanone may be obtained by the method described by MANNICH C., Arch. Pharm., (1917), 255, 261.

3-Hydroxy-2-(7-methoxy-1,8-naphthyridin-2-yl)-1isoindolinone may be prepared according to the method described in Belgian Patent No. 815,019.

EXAMPLE 3

Potassium borohydride (0.41 g) dissolved in distilled water (12 cc) is added at a temperature in the region of 20° C. to a suspension of 2-(7-methoxy-1,8-naphthyridin-2-yl)-3-(5-methyl-2-oxohexyl)-1-isoindolinone (3.0 g) in ethanol (50 cc), and the suspension is stirred for 16 hours at a temperature in the region of 20° C. The reaction mixture is then poured into a mixture of distilled water (300 cc) and dichloromethane (150 cc) which has been cooled to a temperature in the region of 0° C. The aqueous phase is separated after settling has occurred, and re-extracted with dichloromethane (2×150 cc). The organic phases are combined, washed with distilled water (3×25 cc), dried over magnesium sulphate, filtered and then concentrated to dryness under reduced pressure (2.7 kPa) at 40° C. The product obtained is recrystallized twice in diisopropyl ether. 3-(2-Hydroxy-5-methylhexyl)-2-(7-methoxy-1,8-naphthyridin-2-yl)-1-isoindolinone (2.0 g), m.p. 110° C., is thereby obtained.

EXAMPLE 4

Tetrabutylammonium fluoride (11.5 g) is added in small portions at a temperature in the region of 0° C. to a solution of 3-(5-tert-butyldimethylsilyloxy-2-oxopentyl)-2-(7-methoxy-1,8-naphthyridin-2-yl)-1-isoindolinone (9.2 g) in anhydrous tetrahydrofuran (185 cc), and the solution obtained is stirred for 5 minutes at a temperature in the region of 0° C. The reaction mixture is then stirred for 1 hour 30 minutes at a temperature in the region of 20° C. and then poured into a mixture of ice (200 g) and water (600 cc). The insoluble product is separated by filtration, washed successively with water (5×25 cc) and diisopropyl ether (2×10 cc) and dried in the air. After recrystallization in acetonitrile, 3-(5-hydroxy-2-oxopentyl)-2-(7-methoxy-1,8-naphthyridin-2-yl)-1-isoindolinone (5.6 g), m.p. 152° C., is obtained.

3-(5-Tert-butyldimethylsilyloxy-2-oxopentyl)-2-(7-methoxy-1, 8-naphthyridin-2-yl)-1-isoindolinone may be prepared by working in a manner similar to that described in Example 1, but starting with 3-hydroxy-2-(7-methoxy-1,8-naphthyridin-2-yl)-1-isoindolinone (12.4 g), an oily suspension (50% by weight; 3.9 g) of sodium hydride and 5-tert-butyldimethylsilyloxy-2-pentanone (17.6 g). After recrystallization in diisopropyl ether, 3-(5-tert-butyldimethylsilyloxy-2-oxopentyl)-2-(7-methoxy-1, 8-naphthyridin-2-yl)-1-isoindolinone (8.9 g), m.p. 125° C., is obtained.

3-Hydroxy-2-(7-methoxy-1,8-naphthyridin-2-yl)-1-isoindolinone may be prepared by the method described in Belgian Patent No. 815,019.

5-Tert-butyldimethylsilyloxy-2-pentanone may be prepared in the following manner: imidazole (8.5 g) and 5-hydroxy-2-propanone (5.1 g) are added successively at a temperature in the region of 20° C. to a solution, maintained under an argon atmosphere, of chloro-tert-butyldimethylsilane (9.4 g) in anhydrous dimethylformamide (20° cc). The reaction mixture is heated with stirring to a temperature of 35° C. for 15 hours, and then poured into a mixture of ice (40 g) and water (60 cc). The product is then extracted with ethyl acetate (3×80 cc). The organic phases are combined, washed with water (5×10 cc), dried over magnesium sulphate, filtered and concentrated to dryness under reduced pressure (2.7 kPa) at 40° C. ( By distillation of the residue under reduced pressure, 5-tert-butyldimethylsilyloxy-2-pentanone (5 g) is obtained in the form of a colourless liquid, b.p. 69°–70° C. at 0.04 kPa.

EXAMPLE 5

Working in a manner similar to that described in Example 1, but starting with 3-hydroxy-2-(7-methoxy-1,8-naphthyridin-2-yl)-1-isoindolinone (9.2 g), an oily suspension (50% by weight; 2.9 g) of $odium hydride and 1-cyclopropyl-2-propanone (6 g), 3-(3-cyclopropyl-2-oxopropyl)-2-(7-methoxy-1,8-naphthyridin-2-yl)-1-isoindolinone (3.9 g), m.p. 165° C., is obtained after recrystallization in acetonitrile.

1-Cyclopropyl-2-propanone may be prepared by the method described in Japanese Patent 79 73, 757 [Chem. Abstr. (1979), 91, 174895g].

EXAMPLE 6

Working in a manner similar to that described in Example 1, but starting with 3-hydroxy-2-(7-methylthio-1,8-naphthyridin-2-yl)-1-isoindolinone (13.3 g), an oily suspension (50% by weight; 4.1 g) of sodium hydride and 5-methyl-2-hexanone (9.4 g), and stirring the reaction mixture for 4 hours at a temperature in the region of $-5°$ C., 3-(5-methyl-2-oxohexyl)-2-(7-methylthio-1,8-naphthyridin-2-yl)-1-isoindolinone (4.3 g), m.p. 160° C., is obtained after recrystallization in ethyl acetate.

3-Hydroxy-2-(7-methylthio-1,8-naphthyridin-2-yl)-1-isoindolinone may be prepared in the following manner: potassium borohydride (2.8 g) is added in small portions at a temperature in the region of 20° C. to a suspension of 2-(7-methylthio-1,8-naphthyridin-2-yl)-1,3-isoindolinedione (16.6 g) in a mixture of tetrahydrofuran (250 cc) and water (25 cc), and the suspension obtained is stirred for 4 hours at a temperature in the region of 20° C. The reaction mixture is then poured into a mixture of ice (80 g) and water (160 cc) and neutralized with 1 N aqueous hydrochloric acid solution. The insoluble product is separated by filtration, washed with water ($5\times50$ cc) and dried in the air. 3-Hydroxy-2-(7-methylthio-1,8-naphthyridin-2yl)-1-isoindolinone (13 g), m.p. 210° C., is thereby obtained.

2-(7-Methylthio-1,8-naphthyridin-2-yl)-1,3-isoindolinedione may be prepared in the following manner: phthalic anhydride (7.5 g) is added to a suspension of 2-amino-7-methylthio-1,8-naphthyridin (9.6 g) in Dowtherm A (registered trade mark) (275 cc). The reaction mixture is stirred and heated to a temperature of 155° C. for 3 hours, and then cooled to a temperature in the region of 20° C. and treated with diisopropyl ether (175 cc) and stirred for 1 hour. The insoluble product is then separated by filtration, washed with diisopropyl ether ($3\times40$ cc) and dried in the air. 2-(7-Methylthio-1,8-naphthyridin-2-yl)-1,3-isoindolinedione (15.2 g), m.p. 235° C., is thereby obtained.

2-Amino-7-methylthio-1,8-naphthyridin may be prepared as described in the European Patent Application published under No. 172,083.

EXAMPLE 7

Working in a manner similar to that described in Example 1, but starting with 2-(7-chloro-2-quinolyl)-3-hydroxy-1-isoindolinone (6.2 g), an oily suspension (50% by weight; 2 g) of sodium hydrlde and 5-methyl-2-hexanone (4.6 g), and stirring the reaction mixture for 3 hours at a temperature in the region of $-10°$ C., 2-(7-chloro-2-quinolyl)-3-(5-methyl-2-oxohexyl)-1-isoindolinone (1.4 g), m.p. 127° C., is obtained after recrystallization in ethanol.

2-(7-Chloro-2-quinolyl)-3-hydroxy-1-isoindolinone may be prepared by the method described in Belgian Patent No. 793,851.

EXAMPLE 8

Working in a manner similar to that described in Example 1, but starting with 3-hydroxy-2-(7-methoxy-1,8-naphthyridin-2-yl)-1-isoindolinone (6.2 g), an oily suspension (50% by weight; 2 g) of sodium hydride and 1-cyclohexyl-2-propanone (3.1 g), 3-(3-cyclohexyl-2-oxopropyl)-2-(7-methoxy-1,8-naphthyridin-2-yl)-1-isoindolinone (5 g), m.p. 139° C., is obtained after recrystallization in acetonitrile.

1-cyclohexyl-2-propanone may be prepared by the method described by GUERBET M., C. R. Acad. Sc. Paris, (1917), 164, 952.

EXAMPLE 9

Working in a manner similar to that described in Example 1, but starting with 3-hydroxy-2-(7-methoxy-1,8-naphthyridin-2-yl)-1-isoindolinone (9.4 g), an oily suspension (50% by weight; 4.4 g) of sodium hydride and 4-oxo-N,N-dimethylpentanamide (4.8 g), and stirring the reaction mixture for 4 hours at a temperature in the region of 0° C., 5-[2-(7-methoxy-1,8-napthyridin-2-yl)-3-oxo-1-isoindolinyl)]-4-oxo-N, N-dimethylpentanamide (3.1 g), m.p. 184° C., i$ obtained after recrystallization in acetonitrile.

4-Oxo-N,N-dimethylpentanamide may be prepared by the method described by LUKES R., Collect. Czech. Chem. Commun. (1963), 28 (8), 2182.

EXAMPLE 10

Working in a manner similar to that described in Example 1, but starting with 3-hydroxy-2-(7-methoxy-1,8-naphthyridin-2-yl)-1-isoindolinone (3.11 g), an oily suspension (50% by weight; 1 g) of sodium hydride and 6-methyl-2-heptanone (2.6 g), and stirring the reaction mixture for 4 hours at a temperature in the region of $-5°$ C., 2-(7-methoxy-1,8-naphthyridin-2-yl)-3-(6-methyl-2-oxoheptyl)-1-isoindolinone (4.4 g), m.p. 140° C., is obtained after recrystallization in acetonitrile.

6-Methyl-2-heptanone may be prepared by the method described by BRUNIE J. C. and COLONGE J., C. R. Acad. Sc. Paris (1962), 255, 1621.

EXAMPLE 11

Working in a manner similar to that described in Example 1, but starting with 3-hydroxy-2-(7-methoxy-1,8-naphthyridin-2-yl)-1-isoindolinone (3.1 g), an oily suspension (50% by weight; 1 g) of sodium hydride and 4-methyl-2-hexanone (2.4 g), and stirring the reaction mixture for 20 hours at a temperature in the region of 0° C., 2-(7-methoxy-1,8-naphthyridin-2-yl)-3-(4-methyl-2-oxohexyl)-1-isoindolinone (2.2 g), m.p. 120° C., is obtained after recrystallization in acetonitrile.

4-Methyl-2-hexanone may be prepared by the method described by JOHNSON J. R. and HAGER F. D., Org. Synth., Coll. Vol. I, 351.

EXAMPLE 12

Working in a manner similar to that of Example 1, but starting with 3-hydroxy-2-(7-methoxy-1,8-naphthyridin-2-yl)-1-isoindolinone (6.2 g) an oily suspension (50% by weight; 1.92 g) of sodium hydride and 3-methyl-2-hexanone (4.5 g), 2-(7-methoxy-1,8-naphthyridin-2-yl)-3-(3-methyl-2-oxohexyl)-1-isoindolinone (2.1 g), m.p. 86° C., is obtained after two successive recrystallizations in isopropyl ether.

3-Methyl-2-hexanone may be prepared by the method described by JONES E. J., Ann. Chem. Pharm. (1884), 226, 287.

EXAMPLE 13

An oily suspension (50% by weight; 3.1 g) of sodium hydride is added in small portions at a temperature in the region of −5° C. to a solution, maintained under a nitrogen atmosphere, of 3-hydroxy-2-(7-methoxy-1,8-naphthyridin-2-yl)-1-isoindolinone (10 g) in anhydrous dimethylformamide (195 cc), and the suspension obtained is stirred for 30 minutes at a temperature in the region of −5° C. A solution of 2-hexanone (6.5 g) in anhydrous dimethylformamide (5 cc) is then added and stirring is continued for 8 hours at a temperature in the region of 0° C. and then for 16 hours at a temperature in the region of 20° C. The reaction mixture is then poured into water (1.5 litres). The solid obtained is separated by filtration, washed with water and dried in the air. After recrystallization in ethanol, 2-(7-methoxy-1,8-naphthyridin-2-yl)-3-(2-oxohexyl)-1-isoindolinone (3.6 g), m.p. 161° C., is obtained.

EXAMPLE 14

An oily suspension (50% by weight; 3.1 g) of sodium hydride is added at a temperature in the region of −5° C. to a solution, maintained under a nitrogen atmosphere, of 3-hydroxy-2-(7-methoxy-1,8-naphthyridin-2-yl)-1-isoindolinone (10 g) in anhydrous dimethylformamide (180 cc), and the suspension obtained is stirred for 30 minutes at a temperature in the region of 0° C. A solution of cyclohexyl methyl ketone (8.2 g) in anhydrous dimethylformamide (20 cc) is then added and stirring is continued for 6 hours at a temperature in the region of 0° C. and then for 16 hours at a temperature in the region of 20° C. The reaction mixture is then poured into distilled water (800 cc). The solid obtained is separated by filtration, washed with water, dried in the air, and then recrystallized in acetonitrile and finally purified by chromatography under pressure (50 kPa) on silica gel (0.04–0.063 mm; 140 g) contained in a column 2.8 cm in diameter. Elution is performed with methylene chloride, collecting 20-cc fractions. Fractions 25 to 62 are combined and concentrated to dryness under reduced pressure (2.7 kPa) at 40° C. The solid obtained is taken up with ethyl ether (100 cc) and separated by filtration. 3-(2-Cyclohexyl-2- oxoethyl)-2-(7-methoxy-1,8-naphthyridin-2-yl)-1-isoindolinone (4.8 g), m.p. 140° C., is obtained.

EXAMPLE 15

Working as in Example 14, but starting with 3-hydroxy-2-(7-methoxy-1,8-naphthyridin-2-yl)-1-isoindolinone (15 g), an oily suspension (50% by weight, 4.7 g) of sodium hydride and 6-methyl-5-hepten-2-one (12.4 g), 2-(7-methoxy-1,8-naphthyridin-2-yl)-3-(6-methyl-2-oxo-5-heptenyl)-1-isoindolinone (7.6 g), m.p. 160° C., is obtained after recrystallization in ethanol.

EXAMPLE 16

Working as in Example 13, but starting with 3-hydroxy-2-(7-methoxy-1,8-naphthyridin-2-yl)-1-isoindolinone (10 g), an oily suspension (50% by weight; 3.1 g) of sodium hydride and 4-acetyl-1-methylpiperidine (9.2 g), 2-(7-methoxy-1, 8-naphthyridin-2-yl)-3-[2-(1-methyl-4-piperidyl)-2-oxoethyl]-1-isoindolinone (4.8 g), m.p. 172° C., is obtained after recrystallization in ethanol.

4-Acetyl-1-methylpiperidine may be prepared in the following manner: formic acid (3.9 cc) and then a 35% strength aqueous solution (8.2 cc) of formaldehyde are added at a temperature in the region of 5° C. to a solution of 4-acetylpiperidine (5.2 g) in distilled water (10 cc). The reaction mixture is heated to reflux for 4 hours. 1 N aqueous sodium hydroxide solution (50 cc) is then added and the aqueous solution obtained is extracted with methylene chloride (3×60 cc). The organic phases are combined and washed with water (2×40 cc), dried over magnesium sulphate and concentrated to dryness under reduced pressure (2.7 kPa). 4-Acetyl-1-methylpiperidine (1.4 g) is thereby obtained, and this is employed in the crude state in the subsequent syntheses.

EXAMPLE 17

An oily suspension (50% by weight; 4.7 g) of sodium hydride is added at a temperature in the region of 0° C. to a solution, maintained under a nitrogen atmosphere, of 3-hydroxy-2-(7-methoxy-1,8-naphthyridin-2-yl)-1-isoindolinone (15 g) in anhydrous dimethylformamide (280 cc), and the suspension obtained is stirred for 30 minutes at a temperature in the region of 0° C. A solution of benzylacetone (14.4 g) in anhydrous dimethylformamide (20 cc) is added and stirring is continued for 21 hours at a temperature in the region of 0° C. The reaction mixture is then poured into distilled water (1.5 litres). The pH of the aqueous phase is brought to approximately 5 by adding 4 N aqueous hydrochloric acid solution. The product is extracted with methylene chloride (3×500 cc). The organic phases are combined and washed with distilled water (3×80 cc), dried over magnesium sulphate and concentrated to dryness at 40° C. under reduced pressure (2.7 kPa). The oily residue obtained is purified by chromatography under pressure (50 kPa) on silica gel (0.040–0.063 mm; 200 g) contained in a column 2.8 cm in diameter. Elution is performed with methylene chloride, collecting 50-cc fractions. Fractions 9 to 21 are combined and concentrated to dryness at 40° C. under reduced pressure (2.7 kPa). After the solid obtained is recrystallized in ethanol, 2-(7-methoxy-1,8-naphthyridin-2-yl)-3-(2-oxo-4-phenylbutyl)-1-isoindolinone (3.4 g), m.p. 180° C., is obtained.

EXAMPLE 18

Hydroxylamine hydrochloride (0.9 g) is added to a suspension, maintained at 0° C. with a bath of ice-cold water, of 2-(7-methoxy-1,8-naphthyridin-2-yl)-3-(5-methyl-2-oxohexyl)-1-isoindolinone (4.3 g) in a mixture (100 cc) of water and ethanol (50:50 by volume). The suspension obtained is allowed to return to a temperature in the region of 20° C. and a solution of sodium carbonate (0.7 g) in distilled water (10 cc) is added. The suspension obtained is heated to reflux for 22 hours. During this period, ethanol (80 cc) is added in two portions. Refluxing is maintained for 12 hours, adding in three portions further hydroxylamine hydrochloride (1.35 g) and sodium carbonate (1.05 g). The reaction mixture is then poured into water (1 litre). The aqueous phase is extracted with methylene chloride (3×300 cc). The organic phases are combined, washed with distilled water (2×100 cc), dried over magnesium sulphate, filtered and concentrated to dryness. After recrystallization in 2-propanol, 3-(2-hydroxyimino-5-methylhexyl)-2-(7-methoxy-1,8-naphthyridin-2-yl)-1-isoindolinone (1 g), m.p. 200° C., is obtained.

2-(7-Methoxy-1,8-naphthyridin-2-yl)-3-(5-methyl-2-oxohexyl)-1-isoindolinone may be prepared as described in Example 1.

EXAMPLE 19

Working in a manner similar to that described in Example 1, but starting with 3-hydroxy-2-(1,8-naphthyridin-2-yl)-1-isondolinone (4.5 g), an oily suspension (50% by weight; 1.2 g) of sodium hydride and 5-methyl-2hexanone (3.7 g), and stirring the reaction mixture for 3 hours at a temperature in the region of −10° C., 3-(5-methyl-2-oxohexyl)-2-(1,8-naphthyridin-2-yl)-1-isoindolinone (4.1 g), m.p. 166° C., is obtained after recrystallization in ethanol.

3-Hydroxy-2-(1,8-naphthyridin-2-yl)-1-isoindolinone may be prepared by the method described in Belgian Patent No. 815,019.

EXAMPLE 20

Working in a manner similar to that described in Example 1, but starting with 3-hydroxy-2-(7-methyl-1,8-naphthyridin-2-yl)-1-isoindolinone (7.9 g), an oily suspension (50% by weight; 2 g) of sodium hydride and 5-methyl-2-hexanone (6.2 g), and stirring the reaction mixture for 3 hours at a temperature in the region of −5° C., and then for 2 hours at 0° C., 2-(7-methyl-1,8-naphthyridin-2-yl)-3-(5-methyl-2-oxohexyl)-1-isoindolinone (1 g), m.p. 155° C., is obtained after recrystallization in ethanol.

3-Hydroxy-2-(7-methyl-1,8-naphthyridin-2-yl)-1-isoindolinone may be prepared by the method described in Belgian Patent No. 815,019.

EXAMPLE 21

Lithium chloride (6.4 g) and distilled water (3.2 cc) are added at a temperature in the region of 20° C. to a solution, maintained under an argon atmosphere, of ethyl 2-[2-(7-chloro-1,8-naphthyridin-2-yl)-3-oxo-1-isoindolinyl]-6-methyl-3-oxoheptanoate in dimethyl sulphoxide (50 cc). The reaction mixture is heated to reflux for 30 minutes, then cooled to a temperature in the region of 40° C., treated with water (150 cc) and stirred for 1 hour. The solid which precipitates is separated by filtration, washed with water (5×10 cc) and dried in the air. After recrystallization in acetonitrile, 2-(7-chloro-1,8-naphthyridin-2-yl)-3-(5-methyl-2-oxohexyl)-1-isoindolinone (3.3 g), m.p. 180° C., is obtained.

Ethyl 2-[2-(7-chloro-1,8-naphthyridin-2-yl)-3-oxo-1-isoindolinyl]-6-methyl-3-oxoheptanoate may be prepared in the following manner: an oily suspension (50% by weight; 1.73 g) of sodium hydride is added to anhydrous dimethylformamide (150 cc) under an argon atmosphere at a temperature in the region of 0° C. A solution of ethyl 6-methyl-3-oxoheptanoate (8.37 g) in anhydrous dimethylformamide (10 cc) is added and the suspension obtained is stirred for 35 minutes, allowing the temperature to rise to 20° C. 3-Chloro-2-(7-chloro-1,8-naphthyridin-2-yl)-1-isoindolinone (10 g) is then added and stirring is maintained for 6 hours at a temperature in the region of 20° C. The reaction mixture is then poured into water (800 cc). The aqueous phase is acidified to a pH in the region of 6 by means of 1 N aqueous hydrochloric acid solution, and then extracted with dichloromethane (3×300 cc). The organic phases are combined, washed with water (3×200 cc), dried over magnesium sulphate and then concentrated to dryness under reduced pressure (2.7 kPa). After the residue obtained is recrystallized in boiling ethanol (100 cc), ethyl 2-[2-(7-chloro-1,8-naphthyridin-2-yl)-3-oxo-1-isoindolinyl]-6-methyl-3-oxoheptanoate (7 g), m.p. 140° C., is obtained.

Ethyl 6-methyl-3-oxoheptanoate may be prepared by the method described by KOGL F. and SALEMINK C. A., Rec. Trav. Chim. Pays-Bas, (1952), 71, 779.

3-Chloro-2-(7-chloro-1,8-naphthyridin-2-yl)-1isoindolinone may be prepared in the following manner: sulphinyl chloride (200 cc) is added dropwise with stirring to 3-hydroxy-2-(7-methoxy-1,8-naphthyridin-2-yl)-1-isoindolinone (15.5 g). The reaction mixture is heated to reflux with stirring for 1 hour, then treated with dimethylformamide (0.5 cc) and heated again to reflux for 3 hours, then cooled to a temperature in the region of 60° C. and concentrated to dryness under reduced pressure (2.7 kPa), at 60° C. Dichloromethane (100 cc) is added to the residue obtained and the mixture is concentrated to dryness under reduced pressure (2.7 kPa) at 60° C. Dichloromethane (100 cc) is added to the residual solid obtained and the mixture is stirred for 10 minutes. The insoluble product is separated by Filtration and washed with dichloromethane (15 cc) and then with diisopropyl ether (2×25 cc) and dried in the air. 3-Chloro-2-(7-chloro-1,8-naphthyridin-2-yl)-1-isoindolinone (12.4 g), which has not melted at 300° C., is thereby obtained.

EXAMPLE 22

Lithium chloride (7 g) and distilled water (3 cc) are added at a temperature in the region of 20° C. to a solution, maintained under an argon atmosphere, of ethyl 2-[2-(7-chloro-1, 8-naphthyridin-2-yl)-3-oxo-1-isoindolinyl]-4-isopropoxy-3-oxobutanoate (5 g) in anhydrous dimethyl sulphoxide (375 cc), and the reaction mixture is heated to reflux for 30 minutes. After the mixture is cooled to a temperature in the region of 40° C., ice-cold water (800 cc) is added and the product is then extracted with dichloromethane (3×300 cc). The organic phases are combined, washed with water (3×150 cc), dried over magnesium sulphate, filtered and then concentrated to dryness under reduced pressure (2.7 kPa) at 40° C. The oily residue obtained is purified by chromatography on silica (300 g) contained in a column 4 cm in diameter [eluent: dichloromethane/methanol (98:2 by volume)]. Elution is first performed with 400 cc of solvent: the corresponding eluate is discarded; elution is then performed with 1800 cc of solvent: the corresponding eluate is concentrated to dryness under reduced pressure (2.7 kPa) at 40° C. After the residue obtained is recrystallized in acetonitrile, 2-(7-chloro-1,8-naphthyridin-2-yl)-3-(3-isopropoxy-2-oxo-propyl)-1-isoindolinone (2.5 g), m.p. 200° C., is obtained.

Ethyl 2-[2-(7-chloro-1, 8-naphthyridin-2-yl)-3-oxo-1-isoindolinyl]-4-isopropoxy-3-oxobutanoate may be prepared in the following manner: an oily suspension (50% by weight; 2.15 g) of sodium hydride is added in small portions at a temperature in the region of 0° C. to a solution, maintained under an argon atmosphere, of ethyl 4-isopropoxy-3-oxobutanoate (11 g) in anhydrous dimethylformamide (150 cc), and the suspension obtained is stirred for 30 minutes at a temperature in the region of 0° C. A solution of 3-chloro-2-(7-chloro-1,8-naphthyridin-2-yl)-1-isoindolinone (11.8 g) in anhydrous dimethylformamide (100 cc) is then added, and stirring is continued for 3 hours at a temperature in the region of 20° C. The reaction mixture is then heated to a temperature of 60° C. for 30 minutes, then cooled to a temperature in the region of 10° C., poured into water (800 cc) and treated with 1 N aqueous hydrochloric acid solution (45 cc). The product which precipitates is separated by filtration, washed with distilled water (4×100 cc) and dried in the air. After two successive recrystallizations in acetonitrile, ethyl 2-[2-(7-chloro-1, 8-naphthyridin-2-yl)-3-oxo-1-isoindolinyl]-4-isopropoxy-3-oxobutanoate (1.5 g), m.p. 205° C., is obtained.

Ethyl 4-isopropoxy-3-oxobutanoate may be prepared in the following manner: to anhydrous diethyl ether (60 cc) maintained under an argon atmosphere, there is added in small portions, at a temperature in the region of 20° C., an oily suspension (50% by weight; 25 g) of sodium hydride followed by diethyl carbonate (61.4 g), and the reaction mixture is heated to a temperature in the region of 45° C. 1-Isopropoxy-2-propanone (31 g) is added in the course of 2 hours 30 minutes, this temperature being maintained. After a further 1 hour's stirring at this temperature, the reaction mixture is cooled to a temperature in the region of 10° C. and treated successively with ethanol (13 cc), 4 N aqueous hydrochloric acid solution (130 cc) and diethyl ether (400 cc). The aqueous phase is separated after settling has occurred, and re-extracted with diethyl ether (2×200 cc). The organic phases are combined, washed successively with water (50 cc) and saturated aqueous sodium bicarbonate solution (75 cc), and with water (2×50 cc), dried over magnesium sulphate, filtered and then concentrated to dryness under reduced pressure (2.7 kPa) at 40° C. The residue is purified by distillation under reduced pressure. Ethyl 4-isopropoxy-3-oxobutanoate (50.5 g) is thereby obtained in the form of a colourless liquid, b.p. 132°-135° C. at 2.7 kPa.

1-Isopropoxy-2-propanone may be prepared by the method described by HENZE H. R. et al., J. Am. Chem. Soc., (1942), 64, 1223.

EXAMPLE 23

Lithium chloride (4.2 g) and water (1.8 cc) are added at a temperature in the region of 20° C. to a solution, maintained under an argon atmosphere, of methyl 2-[2-(7-chloro-1,8-naphthyridin-2-yl)-3-oxo-1-isoindolinyl]-3-oxo-4-phenylbutanoate (3 g) in dimethyl sulphoxide (230 cc), and the reaction mixture is heated to reflux for 45 minute$. After the mixture is cooled to-a temperature in the region of 40° C., ice-cold water (1500 cc) is added. After 15 minutes α stirring, the solid which precipitates is separated by filtration, washed with distilled water (5×25 cc) and dried in the air. The solid obtained is purified by chromatography on silica gel (140 g) contained in a column 3.4 cm in diameter (eluent: dichloromethane/methanol (98:2 by volume)]. Elution is first performed with 200 cc of solvent: the corresponding eluate is discarded. Elution is then performed with 900 cc of solvent: the corresponding eluate is concentrated to dryness under reduced pressure (2.7 kPa), at 40° C. After recrystallization in acetonitrile, 2-(7-chloro-1,8-naphthyridin-2-yl)-3-(3-phenyl-2-oxopropyl)-1-isoindolinone (1.2 g), m.p. 182° C., is obtained.

Methyl 2-[2-(7-chloro-1, 8-naphthyridin-2-yl)-3-oxo-1-isoindolinyl]-3-oxo-4-phenylbutanoate may be prepared in the following manner: an oily suspension (50% by weight; 2 g) of sodium hydride is added in small portions at a temperature in the region of −5° C. to a solution, maintained under an argon atmosphere, of methyl 3-oxo-4phenylbutanoate (10.1 g) in anhydrous dimethylformamide (130 cc), and the suspension obtained is stirred for 30 minutes at 0° C. A solution of 3-chloro-2-(7-chloro-1,8-naphthyridin-2-yl)-1-isoindolinone (11.6 g) in anhydrous dimethylformamide (100 cc) is then added and stirring is continued for 2 hours at a temperature in the region of 20° C. The reaction mixture is then stirred for 30 minutes at a temperature in the region of 60° C., then poured, after cooling, into water (800 cc), acidified to a pH in the region of 2 by means of 5 N aqueous hydrochloric acid solution and extracted with dichloromethane (3×300 cc). The organic phases are combined, washed with water (4×150 cc), dried over magnesium sulphate, filtered and then concentrated to dryness under reduced pressure (2.7 kPa) at 40° C. After recrystallization in ethanol, methyl 2-[2-(7-chloro-1,8-naphthyridin-2-yl)-3-oxo-1-isoindolinyl]-3-oxo-4-phenylbutanoate (10.1 g), m.p. 185° C., is obtained.

Methyl 3-oxo-4-phenylbutanoate may be prepared by the method described by HUNSDIECKER H., Chem. Ber., (1942), 75, 447.

EXAMPLE 24

Working in a manner similar to that described in Example 21, but starting with ethyl 2-[2-(7-chloro-1, 8-naphthyridin-2-yl)-3-oxo-1-isoindolinyl]-5-methyl-3-oxohexanoate (6.1 g), lithium chloride (8.3 g) and distilled water (4.2 cc), 2-(7-chloro-1,8-naphthyridin-2-yl)-3-(4-methyl-2-oxopentyl)-1-isoindolinone (3.4 g), m.p. 172° C., is obtained after recrystallization in acetonitrile.

Ethyl 2-[2-(7-chloro-1, 8-naphthyridin-2-yl)-3-oxo-1-isoindolinyl]-5-methyl-3-oxohexanoate may be prepared by working in a manner similar to that described in Example 23, but starting with ethyl 5-methyl-3-oxohexanoate (2.6 g), an oily suspension (50% by weight; 0.6 g) of sodium hydride and 3-chloro-2-(7-chloro-1,8-naphthyridin-2-yl)-1-isoindolinone (3.3 g). After recrystallization in diisopropyl ether, ethyl 2-[2-(7-chloro-1, 8-naphthyridin-2-yl)-3-oxo-1-isoindolinyl]-5-methyl-3-oxohexanoate (3.2 g), m.p. 145° C., is thereby obtained.

Ethyl 5-methyl-3-oxohexanoate may be prepared by the method described by KAGAN H. B. and SUEN Y. H., Bull. Soc. Chim. France (1966), 6, 1819.

EXAMPLE 25

Working in a manner similar to that described in Example 21, but starting with ethyl 2-12-(7-chloro-1,8-naphthyridin-2-yl)-3-oxo-1-isoindolinyl]-4-methyl-3-oxopentanoate (7.1 g), lithium chloride (10 g) and distilled water (5.1 cc), 2-(7-chloro-1, 8-naphthyridin-2-yl)-3-(3-methyl-2-oxobutyl)-1-isoindolinone (2.5 g), m.p. 212° C., is obtained after recrystallization in acetonitrile.

Ethyl 2-[2-(7-chloro-1,8-naphthyridin-2-yl)-4-methyl-3-oxopentanoate may be prepared by working in a manner similar to that described in Example 23, but starting with ethyl 4-methyl-3-oxopentanoate (4.7 g), an oily suspension (50% by weight; 1.2 g) of sodium hydride and 3-chloro-2-(7-chloro-1,8-naphthyridin-2-yl)-1-isoindolinone (6.6 g). After recrystallization in diisopropyl ether, ethyl 2-[2-(7-chloro-1, 8-naphthyridin-2-yl)-3-oxo-1-isoindolinyl]-4-methyl-3-oxopentanoate (7 g), m.p. 146° C., is thereby obtained.

Ethyl 4-methyl-3-oxopentanoate may be prepared by the method described by MOUREU C. and DELANGE R., Bull. Soc. Chim. France, (1903), 29 (3), 666.

EXAMPLE 26

Working in a manner similar to that described in Example 21, but starting with ethyl 2-[2-(7-chloro-1, 8-naphthyridin-2-yl)-3-oxo-1-isoindolinyl]-7-methyl-3-oxooctanoate (14.5 g), lithium chloride (18.7 g) and distilled water (9.5 cc), 2-(7-chloro-1, 8-naphthyridin-2-yl)-3-(6-methyl-2-oxoheptyl)-1-isoindolinone (8.7 g), m.p. 157° C., is obtained.

Ethyl 2-[2-(7-chloro-1, 8-naphthyridin-2-yl)-3-oxo-1-isoindolinyl]-7-methyl-3-oxooctanoate may be prepared by working in a manner similar to that described in Example 23, but starting with ethyl 7-methyl-3-oxooctanoate (12 g), an oily suspension (50% by weight; 2.3 g) of sodium hydride and 3-chloro-2-(7-chloro-1,8-naphthyridin-2-yl)-1isoindolinone (13.2 g). After recrystallization in diisopropyl ether, ethyl 2-[2-(7-chloro-1, 8-naphthyridin-2-yl)-3-oxo-1-isoindolinyl]-7-methyl-3-oxooctanoate (11.6 g), m.p. 135° C., is thereby obtained.

Ethyl 7-methyl-3-oxooctanoate may be prepared by the method described by MUKHERJI G. and BARDHAN J. C., J. Chem. Soc., (1963), 2407.

EXAMPLE 27

Working in a manner similar to that described in Example 21, but starting with ethyl 2-[2-(7-chloro-1,8-naphthyridin-2-yl)-3-oxo-1-isoindolinyl]-8-methyl-3-oxononanoate, lithium chloride (17.2 g) and water (8.8 cc), 2-(7-chloro-1,8-naphthyridin-2-yl)-3-(7-methyl-2-oxooctyl) 1-isoindolinone (8.7 g), m.p. 126° C., is obtained after recrystallization in acetonitrile.

Ethyl 2-[2-(7-chloro-1, 8-naphthyridin-2-yl)-3-oxo-1-isoindolinyl]-8-methyl-3-oxononanoate may be prepared by working in a manner similar to that described in Example 23, but starting with ethyl 8-methyl-3-oxononanoate (16.1 g), an oily suspension (50% by weight; 2.9 g) of $odium hydride and 3-chloro-2-(7-chloro-1,8-naphthyridin-2-yl)-1-isoindolinone (16.5 g). After recrystallization in ethanol, ethyl 2-[2-(7-chloro-1, 8-naphthyridin-2-yl)-3-oxo-1-isoindolinyl]-8-methyl-3-oxononanoate (13.7 g), m.p. 136° C., is thereby obtained.

Ethyl 8-methyl-3-oxononanoate may be prepared in the following manner: to anhydrous diethyl ether (250 cc), maintained under an argon atmosphere, there is added in small portions, at a temperature in the region of 0° C., an oily suspension (50% by weight; 48 g) of sodium hydride followed by diethyl carbonate (118 g), and the reaction mixture is heated with stirring to a temperature in the region of 45° C. 7-Methyl-2-octanone (71 g) is then added in the course of 2 hours 30 minutes, this temperature being maintained. After a further 1 hour's stirring at 45° C., the reaction mixture is cooled to a temperature in the region of 10° C. and treated with ethanol (25 cc) followed by 4N aqueous hydrochloric acid solution to a pH in the region of 6. The aqueous phase is separated after settling has occurred, and re-extracted with diethyl ether (3×100 cc). The organic phases are combined, washed with water (2×100 cc), dried over magnesium sulphate, filtered and then concentrated to dryness under reduced pressure (2.7 kPa) at 40° C. The residue is purified by distillation under reduced pressure. Ethyl 8-methyl-3-oxononanoate (78 g) is thereby obtained in the form of a colourless liquid, b.p. 97°-98° C. at 0.13 kPa.

7-Methyl-2-octanone may be prepared by the method described by HEILBRON I. M. JONES E. R. H. and WEEDON B. C. L., J. Chem. Soc., (1944), 140.

EXAMPLE 28

Working in a manner similar to that described in Example 21, but starting with ethyl 2-[2-(7-fluoro-1,8-naphthyridin-2-yl)-3-oxo-1-isoindolinyl]-6-methyl-3-oxoheptanoate (5.2 g), lithium chloride (7.1 g) and distilled water (3.6 cc), 2-(7-fluoro-1,8-naphthyridin-2-yl)3-(5-methyl-2-oxohexyl)-1-isoindolinone (2.8 g), m.p. 162° C., is obtained after recrystallization in ethanol.

Ethyl 2-[2-(7-fluoro-1, 8-naphthyridin-2-yl)-3-oxo-1-isoindolinyl]-6-methyl-3-oxoheptanoate may be prepared by working in a manner similar to that described in Example 23, but starting with ethyl 6-methyl-3-oxoheptanoate (3.8 g), an oily suspension (50% by weight; 0.75 g) of sodium hydride and 3-chloro-2-(7-fluoro-1,8-naphthyridin-2-yl)-1-isoindolinone (4.2 g). After recrystallization in diisopropyl ether, ethyl 2-[2-(7-fluoro-1, 8-naphthyridin-2-yl)-3-oxo-1-isoindolinyl]-6-methyl-3-oxoheptanoate (4 g), m.p. 140° C., is thereby obtained.

Ethyl 6-methyl-3-oxoheptanoate may be prepared according to the method described by KOGL F. and SALEMINK C. A., Rec. Trav. Chim. Pays-Bas (1952), 71, 779. 3-Chloro-2-(7-fluoro-1,8-naphthyridin-2-yl)-1-isoindolinone may be prepared by working in a manner similar to that described in Example 21, but starting with 2-(7-fluoro-1,8-naphthyridin-2-yl)-3-hydroxy-1-isoindolinone (6.6g), sulphinyl chloride (40 cc) and anhydrous dimethylformamide (1.5 cc). 3-Chloro-2-(7-fluoro-1,8-naphthyridin-2-yl)-1-isoindolinone (4.4 g), which has not melted at 265° C., is thereby obtained.

2-(7-Fluoro-1,8-naphthyridin-2-yl)-3-hydroxy-1-isoindolinone may be prepared in the following manner: potassium borohydride (2.3 g) is added in small portions at a temperature in the region of 20° C. to a suspension of 2-(7-fluoro-1,8-naphthyridin-2-yl)-1,3-isoindolinedione (16.6 g) in a mixture of anhydrous methanol (90 cc) and dioxane (90 cc), and the suspension obtained is stirred for 3 hours at a temperature in the region of 20° C. The reaction mixture is then poured into a mixture of ice (120 g) and water (240 cc). The insoluble product is separated by filtration, washed with water (3×50 cc), dried in the air and recrystallized in acetonitrile. 2-(7-Fluoro-1,8-naphthyridin-2-yl)-3-hydroxy-1-isoindolinone (10.3 g), m.p. 246° C., is thereby obtained.

2-(7-Fluoro-1,8-naphthyridin-2-yl)-1,3-isoindolinedione may be prepared in the following manner: potassium fluoride (15 g) i$ added to a suspension, maintained under an argon atmosphere, of 2-(7-chloro-1,8-naphthyridin-2-yl)-1,3-isoindolinedione (20.6 g) in anhydrous nitrobenzene (270 cc), and the reaction mixture is heated to reflux with stirring for 22 hours. After being cooled to a temperature in the region of 80° C., the reaction mixture is concentrated to dryness under reduced pressure (0.13 kPa) at 80° C. The residue obtained is taken up with ethyl acetate (170 cc). The insoluble product is separated by filtration, washed successively with ethyl acetate (30 cc) and water (6×30 cc) and dried in the air. 2-(7-fluoro-1,8-naphthyridin-2-yl)-1,3-isoindolinedionedione (16.9 g), m.p. 264° C., is thereby obtained.

2-(7-Chloro-1,8-naphthyridin-2-yl)-1,3-isoindolinedione may be prepared by the method described in Belgian Patent No. 835,325.

EXAMPLE 29

Working as in Example 21, but starting with ethyl 2-{6-(7-chloro-1, 8-naphthyridin-2-yl)-6,7-dihydro-7- oxo-5H-pyrrolo[3, 4-b]pyrazin-5-yl}-6-methyl-3-oxoheptanoate (8.2 g) in dimethyl sulphoxide (300 cc), lithium chloride (10.6 g) and water (6 cc), 6-(7-chloro-1,8-naphthyridin-2-yl)-6, 7-dihydro-5-(5-methyl-2-oxohexyl)-7-oxo-5H-pyrrolo[3,4-b]pyrazine (5 g), m.p. 247° C., is obtained after recrystallization in acetonitrile.

Ethyl 2-{6-(7-chloro-1, 8-naphthyridin-2-yl)-6,7-dihydro-7-oxo-5H-pyrrolo[3, 4-b]pyrazin-5-yl}-6-methyl-3oxoheptanoate may be prepared in the following manner: sodium (1.1 g) is added to ethanol (400 cc) at a temperature in the region of 0° C. A solution of ethyl 6-methyl-3-oxoheptanoate (10.3 g) in methylene chloride (200 cc) is then added. The solution obtained is stirred for 20 minutes, allowing the temperature to rise to about 20° C. Finally, 5-chloro-6-(7-chloro-1, 8-naphthyridin-2-yl)-6,7-dihydro-7-oxo-5H-pyrrolo[3,4-b]pyrazine (13 g) is added and the reaction mixture is stirred for 5 hours 30 minutes at a temperature in the region of 20° C. The mixture is then diluted with methylene chloride (250 cc) and poured into 4N aqueous sulphuric acid solution (250 cc). After settling has occurred, the aqueous phase is separated and extracted with methylene chloride (100 cc). The organic phases are combined, washed with water (3×100 cc) and 10% strength aqueous sodium bicarbonate solution (100 cc), dried over magnesium sulphate and concentrated to dryness under reduced pressure (2.7 kPa). After the residue obtained is recrystallized in methanol, ethyl 2-{6-(7-chloro-1,8-naphthyridin-2-yl)-6,7-dihydro-7-oxo-5H-pyrrolo[3, 4-b]-pyrazin-5-yl}-6-methyl-3-oxoheptanoate (8.4 g), m.p. 136° C., is obtained.

5-Chloro-6-(7-chloro-1,8-naphthyridin-2-yl)-6, 7-dihydro-7-oxo-5H-pyrrolo[3,4-b]pyrazine may be prepared in the following manner: sulphinyl chloride (300 cc) is added dropwise with stirring to 5-hydroxy-6-(7-methoxy-1,8-naphthyridin-2-yl)-7-oxo-6,7-dihydro-5H-pyrrolo[3, 4-b]pyrazine (23.2 g). The reaction mixture is heated to reflux with stirring for 1 hour, then treated with dimethylformamide (1 cc) and heated again to reflux for 3 hours. After being cooled to a temperature in the region of 60° C., the reaction mixture is concentrated to dryness under reduced pressure (2.7 kPa). The residue obtained is taken up with dichloromethane (100 cc) and the solvent is removed under reduced pressure (2.7 kPa). Dichloromethane (100 cc) is added to the residual solid obtained, and the mixture is stirred for 10 minutes. The insoluble product is separated by filtration and washed with dichloromethane (15 cc) and then with diisopropyl ether (225 cc), and dried in the air. 5-Chloro-6-(7-chloro-1,8-naphthyridin-2-yl)-7-oxo-6,7-dihydro-5H-pyrrolo[3, 4-b]pyrazine (2.1 g), m.p. 264° C., i$ thereby obtained.

5-Hydroxy-6-(7-methoxy-1,8-naphthyridin-2-yl)-7-oxo-6, 7-dihydro-5H-pyrrolo[3,4-b]pyrazine may be prepared by the method described in Belgian Patent No. 815,019.

EXAMPLE 30

Working as in Example 21, but starting with ethyl 2-{6-(7-chloro-1,8-naphthyridin-2-yl)-6, 7-dihydro-7-oxo-5H-pyrrolo[3,4-b]pyrazin-5-yl}-4-methyl-3-oxopentanoate (5.4 g) in dimethyl sulphoxide (200 cc), lithium chloride (7.5 g) and water (4 cc), 6-(7-chloro-1,8-naphthyridin-2-yl)-6, 7-dihydro-5-(3-methyl-2-oxobutyl)-7-oxo-5H-pyrrolo-[3,4-b]pyrazine pyrazine (2.4 g), m.p. 245° C., is obtained after recrystallization in acetonitrile.

Ethyl 2-{6-(7-chloro-1,8-naphthyridin-2-yl)-6, 7-dihydro-7-oxo-5H-pyrrolo[3,4-b]pyrazin-5-yl}-4-methyl-3oxopentanoate may be obtained as in Example 29, but starting with 5-chloro-6-(7-chloro-1,8-naphthyridin-2-yl)-6, 7-dihydro-7-oxo-5H-pyrrolo[3,4-b]pyrazine (13 g), ethyl 4-methyl-3-oxopentanoate (8.7 g), sodium (1.1 g), ethanol (400 cc) and methylene chloride (200 cc). After recrystallization in methanol, ethyl 2-{6-(7-chloro-1, 8-naphthyridin-2-yl)-6,7-dihydro-7-oxo-5H-pyrrolo[3, 4-b]pyrazin-5yl}-4-methyl-3-oxopentanoate (7.8 g), m.p. 214° C., is thereby obtained.

Ethyl 4-methyl-3-oxopentanoate may be prepared by the method described by JACKMAN et al., J. Am. Chem. Soc. 70 2884 (1948).

EXAMPLE 31

A solution of phosphoryl bromide (10.8 g) in dichloromethane (30 cc) is added at a temperature in the region of 20° C. to a solution, maintained under an argon atmosphere, of 2-(7-methoxy-1,8-naphthyridin-2-yl)-3-(5-methyl-2-oxohexyl)-1-isoindolinone (3 g) in dichloromethane (30 cc), and the reaction mixture is heated to reflux for 5 hours and then left stirring at a temperature in the region of 20° C. for 16 hours. The mixture is then poured into ice (50 g), water (100 cc) and dichloromethane (200 cc), and then alkalinized with saturated aqueous sodium carbonate solution to a pH in the region of 10. The aqueous phase is separated after settling has occurred and re-extracted with dichloromethane (100 cc). The organic phases are combined, washed with water (6×50 cc), dried over magnesium sulphate, filtered and then concentrated to dryness under reduced pressure (2.7 kPa). After recrystallization in acetonitrile, 2-(7-bromo-1.8-,naphthyridin-2-yl)-3-(5-methyl-2-oxohexyl)-1-isoindolinone (2.4 g), m.p. 166° C., is obtained.

2-(7-Methoxy-1,8-naphthyridin-2-yl)-3-(5-methyl-2-oxohexyl)-1-isoindolinone may be prepared as described in Example 1.

EXAMPLE 32

A solution of 2-(7-methoxy-1,8-naphthyridin-2-yl)-3-(5-methyl-2-oxohexyl)-1-isoindolinone (16.2 g) in phosphoryl chloride (160 cc) is heated to 100° C. for 6 hours. The mixture is then cooled to a temperature in the region of 50° C. and concentrated to dryness under reduced pressure (2.7 kPa). The residue is treated with ice (150 g) and water (150 g). The mixture is then alkalinized with aqueous ammonia solution (d=0.92) to a pH in the region of 12, and extracted with ethyl acetate (3×300 cc). The organic phases are combined, washed with water (4×100 cc), dried over magnesium sulphate, filtered and then concentrated to dryness under reduced pressure (2.7 kPa). The residue obtained is purified by chromatography on silica (300 g) contained in a column 4 cm in diameter (eluent: dichloromethane). Elution is first performed with 400 cc of solvent: the corresponding eluate is discarded; elution is then performed with 1800 cc of solvent and the corresponding eluate is concentrated to dryness under reduced pressure (2.7 kPa). After the residue obtained is recrystallized in acetonitrile, 2-(7-chloro-1,8-naphthyridin-2-yl)-3-(5-methyl-2-oxohexyl)-1-isoindolinone (6.4 g), m.p. 180° C., is obtained.

2-(7-Methoxy-1,8-naphthyridin-2-yl)-3-(5-methyl-2-oxohexyl)-1-isoindolinone may be prepared as described in Example 1.

EXAMPLE 33

A solution of 2-(7-chloro-1,8-naphthyridin-2-yl)-3-(5-methyl-2-oxohexyl)-1-isoindolinone (26mg) in a 70:30 (v/v) mixture of hexane and ethanol (40cc) is chromatographed on a stationary phase consisting of cellulose tris(phenylcarbamate) adsorbed on macroporous silica gel contained in a column 2.2 cm in diameter and 25cm long. Elution is carried out with a 70:30 (v/v) mixture of hexane and ethanol and is monitored by ultra-violet detection at 360nm. The flow rate is 9 cc/minute. The dextrorotatory isomer is eluted after 20 minutes, followed by the levorotatory isomer. The appropriate eluates are concentrated to dryness under reduced pressure (2.7kPa) at 40° C. to obtain (+)-2-(7-chloro-1, 8-naphthyridin-2-yl)-3-(5-methyl-2-oxohexyl)-1-isoindolinone (9mg), m.p. 172° C. $[\alpha]_D^{20} = +133°(C=1; CH_2Cl_2)$] and (−)-2-(7-chloro-1, 8-naphthyridin-2-yl)-3-(5-methyl-2-oxohexyl)-1-isoindolinone (8mg), m.p. 172° C. $[\alpha]_D^{20} = -129°$ (C=1; $CH_2Cl_2$)].

Racemic 2-(7-chloro-1,8-naphthyridin-2-yl)-3-(5-methyl-2-oxohexyl)-1-isoindolinone may be prepared as described in Example 32.

The present invention also provides pharmaceutical compositions which contain a pyrrole derivative of formula (I) in combination with an adjuvant, a diluent and/or a coating which is compatible and pharmaceutically acceptable. These compositions may be used orally, rectally, parenterally or percutaneously.

As solid compositions for oral administration, tablets, pills, powders (generally in gelatin capsules) or granules may be used. In these compositions, the active product according to the invention is mixed with one or more inert diluents such as sucrose, lactose or starch. These compositions can also contain substances other than diluents, e.g. a lubricant such as magnesium stearate.

As liquid compositions for oral administration, emulsions that are pharmaceutically acceptable, solutions, suspensions, syrups and elixirs containing inert diluents, such as water or liquid paraffin, may be used. These compositions can also contain substances other than diluents, e.g. wetting, sweetening or flavouring products.

The compositions according to the invention for parenteral administration can be suspensions, emulsions or aqueous or non-aqueous sterile solutions. As a solvent or vehicle, it i$ possible to use propylene glycol, a polyethylene glycol, vegetable oils, especially olive oil, or injectable organic esters, e.g. ethyl oleate. These compositions can also contain adjuvants, especially wetting agents, emulsifiers and dispersants. The sterilization may be carried out in several ways, for example using a bacteriological filter, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories which can contain, in addition to the active product, excipients such as cocoabutter or suppo-wax.

The compositions for percutaneous administration are creams, ointments, lotions and linaments, in which the active product is combined with liquid or pasty excipients, preferably in combination with a vehicle which promotes percutaneous migration.

The medicinal products and compositions according to the invention are especially useful in human therapy on account of their anxiolytic, hypnotic, anticonvulsant, antiepileptic and muscle relaxant action.

In human therapy, the doses depend on the effect sought and the period of treatment; they are generally between 10 and 500 mg per day orally for an adult.

In general, the doctor will determine the dosage which he considers most suitable in relation to the age and weight and all other factors particular to the subject to be treated.

The examples which follow, Illustrate compositions according to the invention.

EXAMPLE A

Tablets containing 10-mg doses of active product and having the following composition are prepared according to the usual technique:

| | |
|---|---|
| 2-(7-methoxy-1,8-naphthyridin-2-yl)-3-(5-methyl-2-oxohexyl)-1-isoindolinone | 0.01 g |
| starch | 0.200 g |
| precipitated silica | 0.036 g |
| magnesium stearate | 0.004 g |

Working in the same manner, tablets may be prepared in which the active principle consists of the following products:

2-(7-chloro-1,8-naphthyridin-2-yl)-3-(5-methyl-2-oxohexyl)-1-isoindolinone 2-(7-methoxy-1,8-naphthyridin-2-yl)-3-(2-oxohexyl)-1-isoindolinone 2-(7-methoxy-1,8-naphthyridin-2-yl)-3-(5-methyl-2-oxohexyl)1-isoindolinone 2-(7-methoxy-1,8-naphthyridin-2-yl)-3-(6-methyl-2-oxo-5-heptenyl)-1-isoindolinone 2-(7-methoxy-1,8-naphthyridin-2-yl)-3-(6-methyl-2-oxoheptyl)-1-isoindolinone 3-(3-cyclohexyl-2-oxopropyl)-2-(7-methoxy-1,8-naphthyridin-2-yl)-1-isoindolinone 2-(7-chloro-1,8-naphthyridin-2-yl)-3-(3-isopropoxy-2-oxopropyl)-1-isoindolinone 2-(7-chloro-2-quinolyl)-3-(5-methyl-2-oxohexyl)-1-isoindolinone 2-(7-fluoro-1,8-naphthyridin-2-yl)-3-(5-methyl-2-oxohexyl)-1-isoindolinone.

We claim:

1. A pyrrole derivative of the formula:

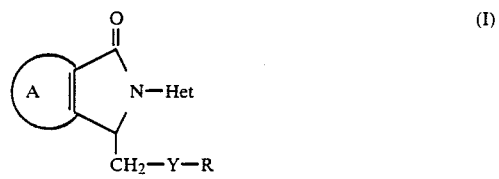

in which A forms with the pyrrole ring a 1-isoindoline ring system, Het denotes a 1, 8-naphthyridine ring system, which is unsubstituted or substituted with a halogen or a (1 to 4 C.) alkyl, (1 to 4 C.) alkyloxy, or (1 to 4 C.) alkylthio radical, Y denotes a CO, C=NOH or CHOH radical and R denotes a straight-or branched-chain alkenyl radical containing 3 to 10 carbon atoms or a straight or branched unsubstituted alkyl radical of 4 to 10 carbon atoms, or an alkyl radical which is substituted by alkyloxy, cyclohexyl or dialkylamino, or phenyl, or R denotes benzyl and, where they exist, "or a pharmaceutically acceptable salt thereof or an optical isomer thereof."

2. A pyrrole derivative according to claim 1 which is 2-(7-chloro-1, 8-naphthyridin-2-yl)-3-(5-methyl-2-oxohexyl)-1-isoindolinone.

3. A pyrrole derivative according to claim 1 which is 2-(7-methoxy-1, 8-naphthyridin-2-yl)-3-(2-oxohexyl)-1-isoindolinone.

4. A pyrrole derivative according to claim 1 which is 2-(7-methoxy-1,8-naphthyridin-2-yl)-3-(5-methyl2-oxohexyl)-1-isoindolinone.

5. A pyrrole derivative according to claim 1 which is 2-(7-methoxy-1,8-naphthyridin-2-yl)-3-(6-methyl2-oxo-5-heptenyl)-1-isoindolinone.

6. A pyrrole derivative according to claim 1 which is 2-(7-methoxy-1,8-naphthyridin-2-yl)-3-(6-methyl-2-oxoheptyl)-1-isoindolinone.

7. A pyrrole derivative according to claim 1 which is 3-(3-cyclohexyl-2-oxopropyl)-2-(7-methoxy-1,8-naphthyridin-2-yl)-1-isoindolinone.

8. A pyrrole derivative according to claim 1 which is 2-(7-chloro-1,8-naphthyridin-2-yl)-3-(3-isopropoxy-2-oxopropyl)-1-isoindolinone.

9. A pyrrole derivative according to claim 1 which is 2-(7-fluoro-1,8-naphthyridin-2-yl)-3-(5-methyl-2-oxohexyl)-1-isoindolinone.

10. A pyrrole derivative according to claim 1 which is the dextrorotary isomer of 2-(7-chloro-1, 8-naphthyridin-2-yl)-3-(5-methyl-2-oxohexyl)-1isoindolinone.

11. Method of producing an anxiolytic, hypnotic, anticonvulsant, antiepileptic or muscle relaxant therapeutic effect in a subject in which such therapy is desirable which comprises administering to said subject an effective amount of a pyrrole derivative according to claim 1.

12. A pharmaceutical composition useful as an anxiolytic, hypnotic, anti-convulsant, antiepileptic or muscle relaxant, which contains, in combination with one or more diluents or adjuvants which are compatible and pharmaceutically acceptable, at least one pyrrole derivative of the formula:

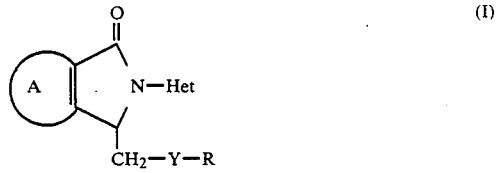

in which A forms with the pyrrole ring an isoindoline ring-system, Het denotes a naphthyridinyl radical, which is unsubstituted or substituted with a halogen or a (1 to 4 C.) alkyl, (1 to 4 C.) alkyloxy, or (1 to 4 C.) alkylthio radical, Y denotes a CO, C=NOH or CHOH radical and R denotes a straight-or branched-chain alkenyl radical containing 3 to 10 carbon atoms or a straight or branched unsubstituted alkyl radical of 4 to 10 carbon atoms, or an alkyl radical which is substituted by alkyloxy, cyclohexyl or dialkylamino, or phenyl, or R denotes benzyl and, where they exist, "or a pharmaceutically acceptable salt thereof or an optical isomer thereof."

* * * * *